United States Patent
Reichert et al.

(10) Patent No.: US 10,243,321 B2
(45) Date of Patent: Mar. 26, 2019

(54) LASER DIODE PACKAGE

(71) Applicant: TRIA Beauty, Inc., Dublin, CA (US)

(72) Inventors: Patrick Reichert, Dublin, CA (US); Harvey I-Heng Liu, Fremont, CA (US)

(73) Assignee: CHANNEL INVESTMENTS, LLC, Tampa, FL (US)

( * ) Notice: Subject to any disclaimer, the term of this patent is extended or adjusted under 35 U.S.C. 154(b) by 957 days.

(21) Appl. No.: 14/154,419

(22) Filed: Jan. 14, 2014

(65) Prior Publication Data

US 2014/0200636 A1   Jul. 17, 2014

Related U.S. Application Data

(60) Provisional application No. 61/752,637, filed on Jan. 15, 2013.

(51) Int. Cl.
*H01S 5/024* (2006.01)
*A61N 5/06* (2006.01)
(Continued)

(52) U.S. Cl.
CPC ........ *H01S 5/02476* (2013.01); *A61N 5/0616* (2013.01); *A61N 2005/067* (2013.01);
(Continued)

(58) Field of Classification Search
CPC ............ H01S 5/02476; H01S 5/02264; H01S 5/02272; H01S 5/02469; H01L 23/051;
(Continued)

(56) References Cited

U.S. PATENT DOCUMENTS 5,825,047 A * 10/1998 Ajisawa .................. G02F 1/025
                                                                  257/12
6,097,744 A    8/2000 Takigawa et al. .............. 372/34
(Continued)

FOREIGN PATENT DOCUMENTS

JP    2005142224 A    6/2005    ............. H01S 5/022
JP    2007019265 A    1/2007    ............... H01S 5/22

OTHER PUBLICATIONS

Liu, Xingsheng et al., "A Study on the Reliability of Indium Solder Die Bonding of High Power Semiconductor Lasers," Journal of Applied Physics, vol. 100, 11 pages, Jul. 6, 2006.
(Continued)

*Primary Examiner* — Aaron F Roane
(74) *Attorney, Agent, or Firm* — Slayden Grubert Beard PLLC

(57) ABSTRACT

A laser package for use in a dermatological treatment device may include a conductive carrier, an insulation layer arranged over a first region of a first side of the conductive carrier, a semiconductor laser device mounted to a second region of the first side of the conductive carrier, and a conductive film secured to the semiconductor laser device and extending over at least a portion of the insulation layer, such that the conductive film is insulated from the conductive carrier by the insulation layer, and wherein a coefficient of thermal expansion of the semiconductor laser device differs from a coefficient of the conductive carrier to which it is mounted by more than 20%.

19 Claims, 8 Drawing Sheets

(51) Int. Cl.
*H01L 23/051* (2006.01)
*H01S 5/022* (2006.01)
*A61N 5/067* (2006.01)

(52) U.S. Cl.
CPC .... *H01L 23/051* (2013.01); *H01L 2924/0002* (2013.01); *H01S 5/02264* (2013.01); *H01S 5/02272* (2013.01); *H01S 5/02469* (2013.01)

(58) Field of Classification Search
CPC .......... H01L 2924/0002; A61N 5/0616; A61N 2005/067
USPC .......................................................... 607/89
See application file for complete search history.

(56) References Cited

U.S. PATENT DOCUMENTS

| | | | | |
|---|---|---|---|---|
| 7,452,356 | B2 | 11/2008 | Grove et al. ...................... | 606/9 |
| 2004/0080042 | A1* | 4/2004 | Macomber ............ | H01L 23/367 |
| | | | | 257/718 |
| 2009/0325344 | A1* | 12/2009 | Takiar ..................... | H01L 24/05 |
| | | | | 438/109 |
| 2010/0260226 | A1 | 10/2010 | Tamaya et al. ............. | 372/50.12 |
| 2012/0289948 | A1* | 11/2012 | Youngquist .......... | A61B 18/203 |
| | | | | 606/9 |

OTHER PUBLICATIONS

International Search Report and Written Opinion, Application No. PCT/US2014/011588, 13 pages, dated Apr. 17, 2014.

\* cited by examiner

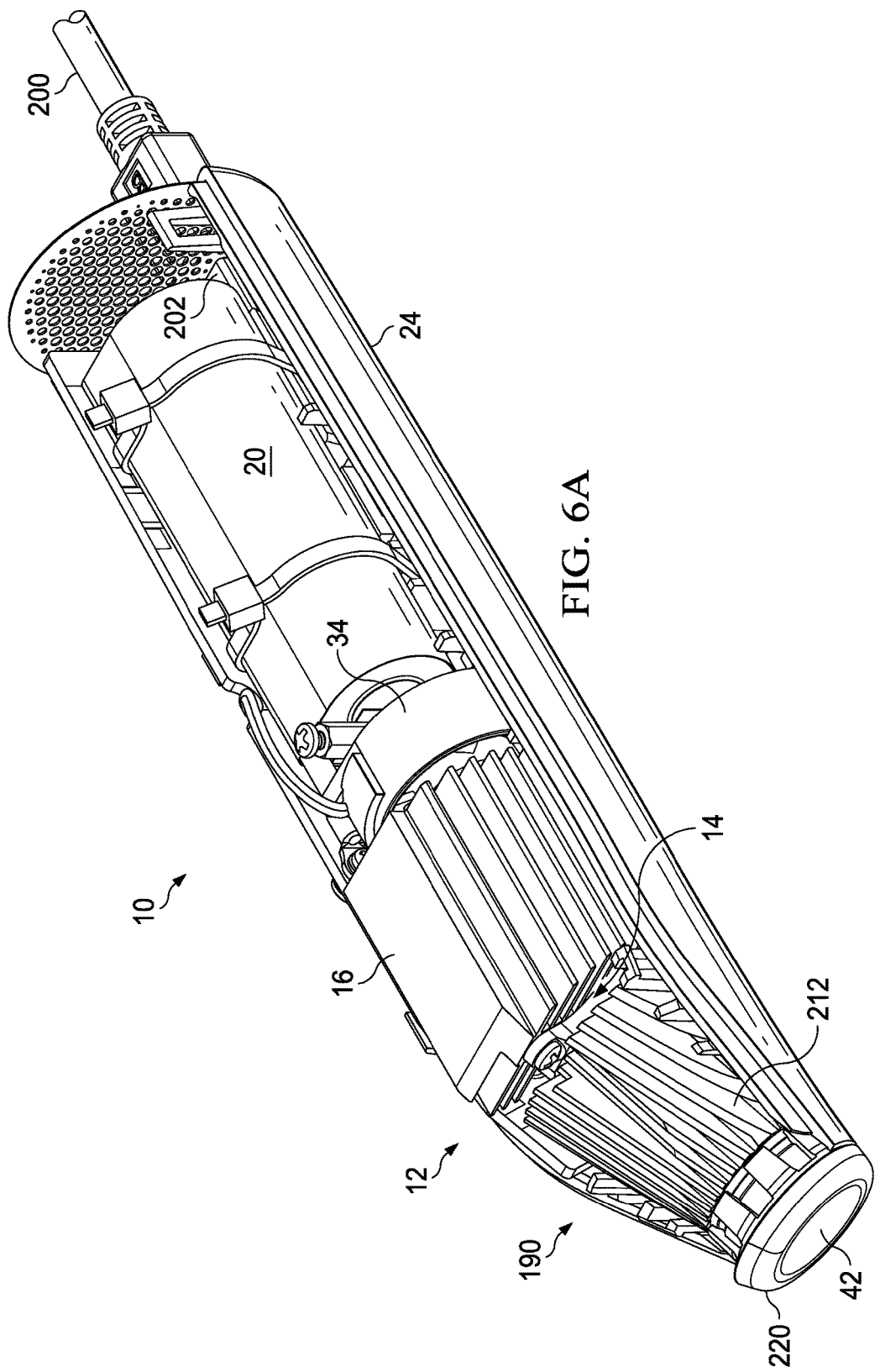

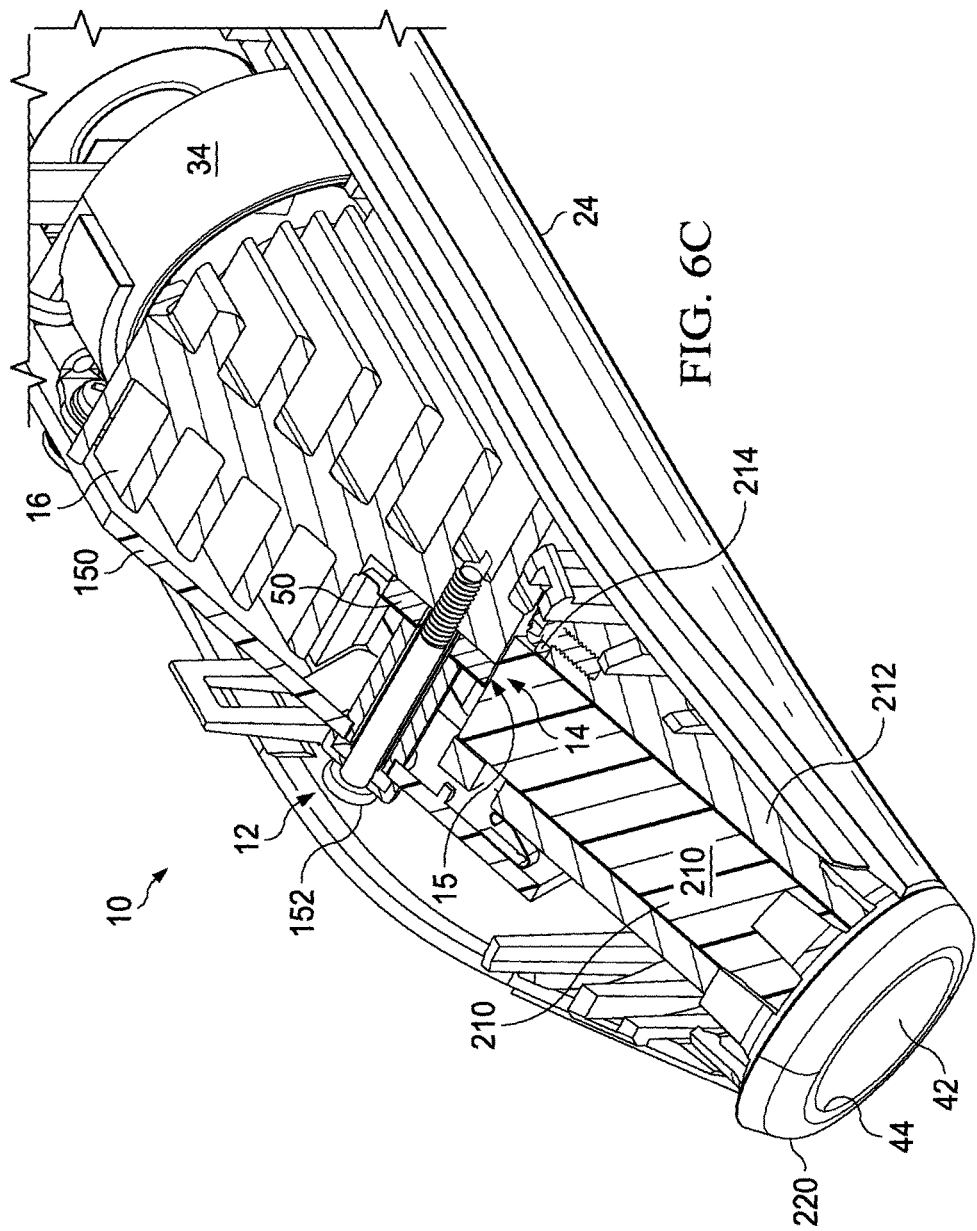

LASER DIODE PACKAGE

CROSS-REFERENCE TO RELATED APPLICATIONS

This application claims the benefit of U.S. Provisional Application No. 61/752,637 filed on Jan. 15, 2013, which disclosure is herein incorporated by reference in its entirety.

TECHNICAL FIELD

The present disclosure is related to a laser diode package, e.g., for use in a laser-based dermatological treatment device.

BACKGROUND

Laser-based treatment of tissue is used for a variety of applications, such as hair removal, skin rejuvenation, wrinkle treatment, acne treatment, treatment of vascular lesions (e.g., spider veins, diffuse redness, etc.), treatment of cellulite, treatment of pigmented legions (e.g., age spots, sun spots, moles, etc.), tattoo removal, and various other treatments. Such treatments generally include delivering laser radiation to an area of tissue on a person's body, e.g., the skin or internal tissue, to treat the tissue in a photochemical, photobiological, thermal, or other manner, which can be ablative or non-ablative, among other properties, depending on the particular application.

Laser-based treatment devices may include any suitable type of laser, e.g., laser diode, fiber laser, VCSEL (Vertical Cavity Surface Emitting Laser), LED, etc. A device may include a single laser or multiple lasers, e.g., a laser diode bar including multiple distinct emitters arranged in a row, or multiple fiber lasers arranged in a row or array.

Diode lasers are particularly suitable for certain treatments and devices for providing such treatments. For example, diode lasers are compact, as they are typically built on one chip that contains all necessary components. Further, diode lasers typically provide an efficiency of up to 50%, which enables them to be driven by low electrical power compared to certain other lasers. Further, diode lasers allow direct excitation with small electric currents, such that conventional transistor based circuits can be used to power the laser.

Other characteristics of diode lasers include high temperature sensitivity/tunability, and a highly divergent beam compared to certain other lasers. Diode lasers typically emit a beam having an axis-asymmetric profile in a plane transverse to the optical axis of the laser. In particular, the emitted beam diverges significantly faster in a first axis (referred to as the "fast axis") than in an orthogonal second axis (referred to as the "slow axis"). In contrast, other types of lasers, e.g., fiber lasers, typically emit a beam having an axis-symmetric profile in the transverse plane.

Laser-based treatment devices include larger-scale devices typically operated by a physician or other professional in a clinic or other office, as well as hand-held devices for home-use, allowing users to provide treatment to themselves. Some hand-held laser-based treatment devices are battery powered, e.g., using a Li ion battery cell (or multiple cells). Such battery-powered devices may be recharged between use, e.g., by plugging into an A/C wall outlet, either directly or by docking in a docking unit plugged into the wall.

Laser-based treatment devices typically provide a laser package for mounting the laser(s), providing power to the laser(s), and removing heat generated by the laser(s), e.g., by providing a thermal coupling to a heat sink or other thermal system. Single-emitter laser diodes and laser diode bars are commonly mounted on carriers or submounts that have a relatively low coefficient of thermal expansion (CTE) to match the CTE of the semiconductor material of the laser, while also exhibiting good thermal conductivity. Two common materials that are CTE-matched to the laser semiconductor, and provide good thermal conductivity, are CuW and BeO. These materials reduce or minimize stress on the laser semiconductor that can cause undesirable optical properties, such as polarization changes, as well as undesirable physical properties such as bar smile, wavelength shift, and bar cracking. Bar cracking typically results in complete failure of the laser. The criticality of changes in polarization, bar smile, and wavelength shift depend on the particular application. These materials (CuW and BeO) are generally not considered low cost due to their intensive fabrication process.

Further, problems exist with certain conventional laser-submount solder connections. For example, a soft solder like Indium is commonly used to act as a compliant layer between a semiconductor laser and the carrier/submount. However, Indium solders may exhibit thermal and electro migration (e.g., the solder material may physically flow out from the solder joint, and may block the laser emitter(s) and thus result in device failure), especially in pulsed laser operations, e.g., employing multi-hundred millisecond pulses.

SUMMARY

Embodiments of the present disclosure provide a laser package with reduced or minimal cost components, readily available materials, and a low cost manufacturing method, while maintaining desired laser performance and reliability for providing a selected laser-based dermatologic treatment, e.g., hair removal or a fractional photothermolysis treatment. Other embodiments provide treatment devices that incorporate such a laser package. Some embodiments operate the laser in a pulsed manner, e.g., for applications that require lifetimes on the order of hundreds of thousands of pulses, for example.

One embodiment of the present disclosure provides a dermatological treatment device including a power supply and a laser package. The laser package may include a conductive carrier (or submount), an insulation layer arranged over a first region of a first side of the conductive carrier, a semiconductor laser device mounted to a second region of the first side of the conductive carrier, and a conductive film (e.g., a foil) secured to the semiconductor laser device and extending over at least a portion of the insulation layer, such that the conductive film is insulated from the conductive carrier by the insulation layer, wherein a coefficient of thermal expansion of the semiconductor laser device differs from a coefficient of the conductive carrier to which it is mounted by more than 20%, wherein the semiconductor laser device is electrically coupled to the power supply via the conductive carrier and the conductive film.

Another embodiment of the present disclosure provides a laser package for use in a dermatological treatment device. The laser package may include a conductive carrier, an insulation layer arranged over a first region of a first side of the conductive carrier, a semiconductor laser device mounted to a second region of the first side of the conductive carrier, and a conductive film secured to the semiconductor laser device and extending over at least a portion of the insulation layer, such that the conductive film is insulated from the conductive carrier by the insulation layer, and wherein a coefficient of thermal expansion of the semiconductor laser device differs from a coefficient of the conductive carrier to which it is mounted by more than 20%.

Another embodiment of the present disclosure provides a method for forming a laser package for a dermatological treatment device. The method includes forming a laser package structure by: providing a conductive having a first coefficient of thermal expansion, arranging an insulation layer over a first region of a first side of the conductive carrier, arranging a first layer of solder preform over a second region of the first side of the conductive carrier, arranging a semiconductor laser device on the first layer of solder preform, arranging a second layer of solder preform over the semiconductor laser device, the semiconductor laser device having a second coefficient of thermal expansion, arranging a conductive film over the second layer of solder preform and extending over at least a portion of the insulation layer, such that the conductive film is insulated from the conductive carrier by the insulation layer, and heating the laser package structure to form (a) a first solder joint between the semiconductor laser device and the conductive carrier and (b) a second solder joint between the conductive film and the semiconductor laser device.

In some embodiments, the carrier may be made of common low cost materials, e.g., Al (plated with Ni for solderability) or Cu, as opposed to more expensive and unique materials such as copper tungsten, beryllium oxide, or aluminum nitride. The laser (e.g., a laser diode or laser diode bar) may be attached on one side to the carrier via solder, while the conductive film or foil (i.e., cathode) may be soldered to the opposite side of the laser, e.g., using a pair of tin-lead solders. The solder joints may be formed in a single step or two-step process. In the case of a two-step process, the solder attaching the foil to the bar may be a lower temperature solder so as to prevent the previous solder joint between the laser bar and the carrier from re-melting. Diode bars with varying widths and varying cavity lengths may be attached to these types of carriers. The conductive film may be stamped, laser cut, or chemically etched, all of which are low-cost, high-volume manufacturing processes. The insulation layer may be a thin sheet of Kapton tape or Kapton shim. Kapton tape may be applied to the carrier prior to soldering, thus resulting in a complete assembly after the solder process and eliminating the need to bend the conductive foil in order to apply the tape, which may cause unwanted stress on the laser bar. Kapton tape's max temperature of 400° C. can easily withstand tin-lead solders temperatures of approximately 230-250° C.

Embodiments of the disclosed laser package may provide various advantage over certain conventional designs. For example, some embodiments may use a carrier that is non-CTE matched to the semiconductor laser (e.g., an aluminum or copper carrier), which may reduce costs compared to conventional designs using expensive CTE-matched materials. As another example, some embodiments may use low cost readily available components for isolation, e.g., Kapton tape.

As another example, some embodiments may provide a low cost fabrication processes, such as batch processing. As another example, some embodiments may allow assembly using a single-step solder process, e.g., to form solder connections on the anode and cathode sides of the laser in a single heating step.

As another example, some embodiments may provide electrical contacts directly integrated onto an associated printed circuit board, e.g., using an electronics circuit board with soldered screw/nut lead contacts.

As another example, the solder thickness between the laser and carrier may be sufficient to avoid any problems caused by surface roughness and/or flatness variations of the underlying carrier. For example, the solder thickness may be between 10 µm and 100 µm, e.g., between 30 µm and 50 µm. This may provide an advantage over certain conventional designs that use an Indium-based solder layer having a thickness (e.g., approximately 5 µm) that may be less than the surface roughness and/or flatness variations in the carrier.

BRIEF DESCRIPTION OF THE DRAWINGS

Some embodiments of the disclosure may be understood by referring, in part, to the following description and the accompanying drawings wherein:

FIGS. 6A-6C show an example laser hair removal device including the example laser engine shown in FIGS. 5A and 5B.

DETAILED DESCRIPTION OF THE DRAWINGS

Some embodiments of the disclosure may be understood by referring, in part, to the following description and the accompanying drawings, in which like reference numbers refer to the same or like parts.

Figure 1:
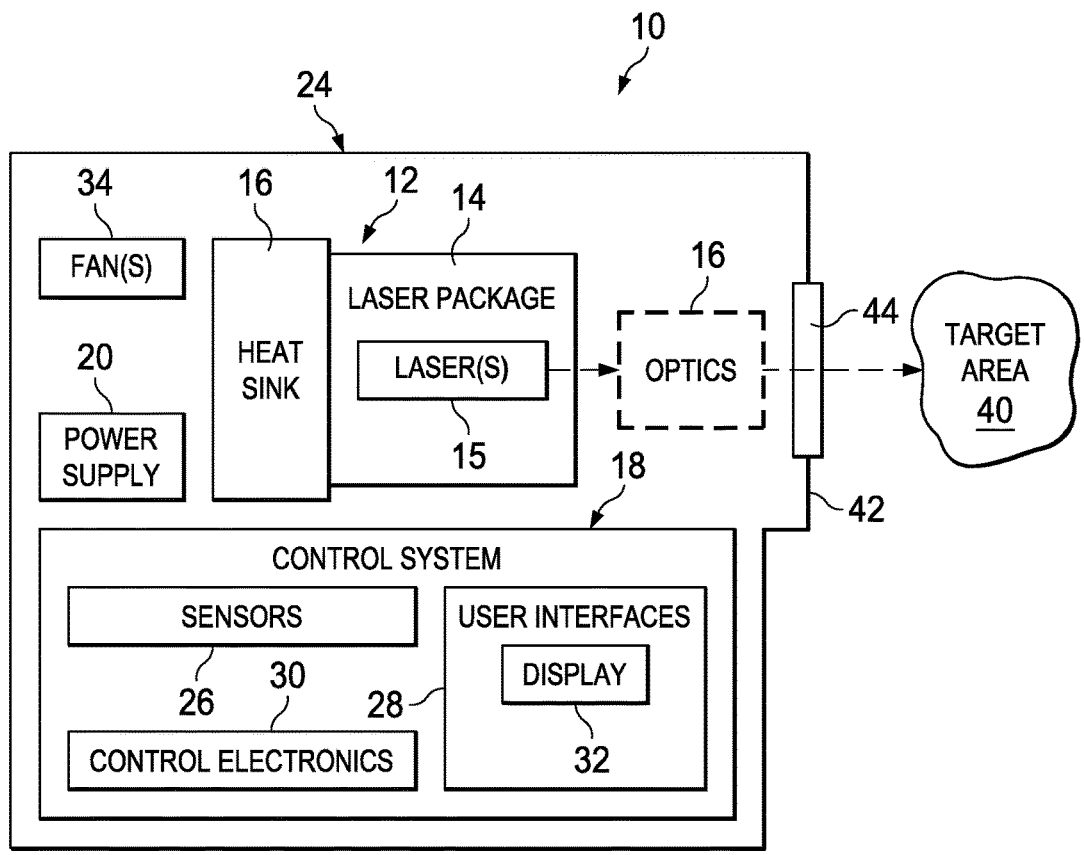
FIG. 1 illustrates components of an example laser-based treatment device including a laser package according to certain embodiments.

FIG. 1 illustrates components of an example treatment device 10, according to certain embodiments. Treatment device 10 may include a laser engine 12 configured to generate one or more laser beams, (optional) optics 18 for delivering the laser beam(s) to a target area 40 (e.g., an area of tissue), a control system 20, one or more power supplies 20, and one or more fans 34.

The components of device 10 may be provided in a structure or housing 24, or alternatively may be provided in separate structures or housings and connected in any suitable manner, e.g., via fiber optic or other cabling. Housing 24 may define an application end (or "treatment tip") 42 configured to be placed in contact with the target surface (e.g., skin) during treatment of the target area 40. Application end 42 may include or house various user interfaces, including the treatment delivery interface for delivering output beams to the user, as well as one or more sensors 26 for detecting various characteristics of the target surface and/or treatment delivered by device 10. In some embodiments, application end 42 may include an aperture or window 44 through which the laser beam is delivered to the target surface, or alternatively, an optical element 18 (e.g., a lens or diffuser) may be located at application end 42 and configured for direct contact or very close proximity with the skin during treatment.

Device 10 may include any other components suitable for providing any of the functionality discussed herein or other related functionality known to one of ordinary skill in the art.

Laser engine 12 may include a laser package 14 including one or more lasers 15 configured to generate one or more laser beams for delivery to the skin, and a heat sink 16 for managing heat produced by the laser(s) 15 and/or other components of device 10, e.g., particular heat-generating control electronics 30. Heat sink 16 may be a separate structure from laser package 14, or may be integrated into laser package 14 (e.g., a carrier or submount of the laser package may act as the heat sink). In some embodiments, heat sink 16 may be cooled by one or more fans 34, e.g., to increase convective heat transfer away from device 10. Laser engine 12 may also include electrical connections and/or electronics for providing power to, and controlling the operation of, laser(s) 15. For example, laser engine 12 may include control electronics 30 of control system 18 (discussed below), such that laser engine 12 and control system 18 are at least partially integrated.

Laser(s) 15 may include any one or more types and numbers of laser devices. For example, laser(s) 15 may include one or more single-emitter or dual-emitter laser diodes, or one or more laser diode bars. Laser(s) 15 may be configured for and/or operated at any suitable wavelength to provide the desired treatment. For example, laser(s) 15 may be configured for and/or operated at a wavelength of about 810 nm (e.g., 810 nm±30 nm) for providing hair removal treatment. As another example, laser(s) 15 may be configured for and/or operated at a wavelength that is absorbed by water in the skin, e.g., between 1400 nm and 2000 nm, e.g., for certain photothermolysis treatments. In some embodiments, laser(s) 15 may be configured for and/or operated at a wavelength of between 1400 nm and 1550 nm, e.g., for acne treatment or certain fractional non-ablative skin treatments. In other embodiments, laser(s) 15 may be configured for and/or operated at a wavelength of between 1700 nm and 1800 nm, e.g., for sebaceous gland related treatment like acne. In still other embodiments, laser(s) 15 may be configured for and/or operated at a wavelength of between 1900 nm and 1950 nm, e.g., for pigmented lesion treatment like solar lentigo.

Further, laser(s) 15 may be configured or operated to deliver continuous wave (CW) radiation, pulsed radiation, or in any other manner. In some embodiments, device 10 controls laser(s) 15 to provide CW radiation, e.g., for using device 10 in a gliding mode for hair removal, bulk heating skin tightening, or acne treatment. In other embodiments, device 10 controls laser(s) 15 to provide user-triggered pulsed radiation, e.g., for using device 10 in a stamping mode for hair removal. In still other embodiments, device 10 controls laser(s) 15 to provide automatically pulsed radiation, e.g., for using device 10 in a gliding mode for hair removal or selective photothermalysis. For example, in some embodiments, device 10 may be configured to sequentially deliver a series of laser beams to the target area 40 to generate overlapping treatment spots, edge-to-edge adjacent treatment spots, or spaced-apart treatment spots (fractional treatment) on the skin, e.g., for a hair removal treatment, skin rejuvenation, wrinkle treatment, treatment of pigmented legions, etc.

Laser(s) 15 may be pulsed with any suitable pulse duration and radiation profile. For example, certain embodiments configured for hair removal may pulse laser(s) 15 with a pulse duration of 50-700 ms. As another example, certain embodiments configured for providing fractional treatment (e.g., for skin rejuvenation or wrinkle treatment) may pulse laser(s) 15 with a pulse duration of 1-20 ms.

Some embodiments of device 10 include one or more optics 18 downstream of laser(s) 15 for directing or treating the beam(s) emitted by laser(s) 15 before reaching the target surface. Optics 18 may include any number and types of optical elements, e.g., lenses, mirrors, diffusers, and other reflective and/or fully or partially transmissive elements or surfaces, for delivering the light generated by laser engine 12 to the target area 40 and, if desired, for treating the beam, such as adjusting the treatment zone size, intensity, treatment zone location, angular distribution, coherence, etc. In some embodiments, optics 18 may include an automated scanning system for scanning a pattern of treatment zones in the target area 40, e.g., as disclosed in application U.S. Ser. No. 13/443,717 filed Apr. 10, 2012, the contents of which application are hereby incorporated in their entirety.

As used herein, an "optic" or "optical element" may mean any element that deflects a light beam, influences the angular distribution profile (e.g., angle of convergence, divergence, or collimation) of a laser beam in at least one axis, influences the focus of the beam in at least one axis, or otherwise affects a property of the radiation. Thus, optics include mirrors and other reflective surfaces, lenses, prisms, light guides, reflective mixing chambers, gratings, filters, diffusers, etc. For the purposes of this disclosure, optics do not generally include planar or substantially planar transmissive elements such as transmissive windows or films, such as those that serve as transmissive aperture that protect internal components.

One example embodiment configured for hair removal includes a cylindrical solid light guide, or mixer, downstream of the laser, which light guide may be surrounded along its length by a reflective cylindrical surface, e.g., a reflective outer coating may be applied to the exterior of the light guide, or the light guide may be received in a cylindrical opening formed in an outer member (e.g., heat sink) that defines a reflective surface around the light guide. The light guide may be arranged such that laser radiation from laser 15 is radiated into an input end of the light guide, and becomes distributed or "mixed" within the light guide such that the radiation is substantially uniformly distributed across the opposite, output end of the light guide. In some embodiments, radiation may be emitted from the output end of the light guide and to the target surface (skin). In other embodiments, one or more additional optics, e.g., a diffuser, lens, or other optic(s), may be arranged downstream of the output end of the light guide. For example, a diffuser may be arranged over the output end of the light guide, and configured to further diffuse the radiation from the light guide, e.g., to provide a further degree of eye safety for radiation emitted from device 10, e.g., a diffuser as disclosed in U.S. Pat. No. 7,452,356, which is hereby incorporated by reference.

In other embodiments, a hollow mixer (e.g., a cylindrical tube) with reflective inner walls may be used instead of a solid light guide, which may similarly act to distribute or "mix" the radiation emitted by laser 15. In some embodiments, the output end of the hollow mixer may be open, or covered by a transmissive window or film. In other embodiments, one or more optics, e.g., a diffuser, lens, or other optic(s), may be arranged at or downstream of the output end of the hollow mixer. For example, a diffuser may be arranged over the output end of the hollow mixer, and configured to further diffuse the radiation from the light guide, e.g., similar to the arrangement disclosed in U.S. Pat. No. 7,452,356, which is hereby incorporated by reference.

Other embodiments of device 10 do not include any optics 18 downstream of laser 15. Such embodiments have an open treatment aperture, or may include a window, e.g., to protect the laser emitter(s) and/or other internal components of the device. A window may be formed from any suitable material, e.g., sapphire, quartz, diamond, or other material transparent at the frequency of the laser(s) 15 and preferably also having a good thermal coefficient.

Control system 20 may include one or more sensors 26, user interfaces 28 for facilitating user interaction with device 10, and control electronics 30 for processing data (e.g., from sensors 26 and/or user interfaces 28) and generating control signals for controlling various components of device 10. Control electronics 30 may include one or more processors and memory devices for storing logic instructions or algorithms or other data. Memory devices may include any one or more device for storing electronic data (including logic instructions or algorithms), such as any type of RAM, ROM, Flash memory, or any other suitable volatile and/or non-volatile memory devices. Logic instructions or algorithms may be implemented as software, firmware, or any combination thereof. Processors may include any one or more devices, e.g., one or more microprocessors and/or microcontrollers, for executing logic instructions or algorithms to perform at least the various functions of device 10 discussed herein. Control electronics 30 may include exclusively analog electronics or any combination of analog and digital electronics.

Control system 20 may control components or aspects of device 10 based on feedback from sensors 26, user input received via user interfaces 28, and/or logic instructions/algorithms. For example, control system 20 may control laser engine 12 and/or a rotating scanning element based on signals from a displacement sensor indicating that device 10 has moved a certain distance across target area 40 from a prior treatment position. As another example, control system 20 may control the operation of laser engine 12 and/or component(s) of a beam scanning system (e.g., a rotating scanning element) based at least on feedback from a glide speed sensor for detecting the speed of device 10 moving across the skin.

More specifically, control system 20 may be configured to control one or more operational parameters of device 10. For example, control system 20 may control the treatment level (e.g., low power level, medium power level, or high power level) or treatment mode (e.g., gliding mode vs. stamping mode; or manually pulsed mode vs. automatically pulsed mode; or rapid-pulse mode vs. slow-pulse mode; or initial treatment mode vs. subsequent treatment mode; etc.), the status of each laser 15 (e.g., on/off, pulse-on time, pulse-off time, pulse duty cycle, pulse frequency, temporal pulse pattern, etc.), parameters of the radiation (e.g., radiation wavelength, intensity, power, fluence, etc.), the configuration or operation of one or more optical elements (e.g., the operation of a rotating-element beam scanning system 142, as discussed below), and/or any other aspects of device 10.

Sensors 26 may include any one or more sensors or sensor systems for sensing or detecting data regarding device 10, the user, the operating environment, or any other relevant parameters. For example, sensors 26 may include one or more of the following types of sensors: (a) one or more displacement sensor for determining the displacement of device 10 relative to the skin as device 10 is moved (e.g., glided) across the skin, (b) one or more glide speed sensor for determining the speed, rate, or velocity of device 10 moving (e.g., gliding) across the skin, (c) one or more skin-contact sensor for detecting proper contact between device 10 and the skin, (d) one or more pressure sensor for detecting the pressure of device 10 pressed against the skin, (e) one or more temperature sensor for detecting the temperature of the skin, a region of the skin, and/or components of device 10, (f) one or more radiation sensor for detecting one or more parameters of radiation (e.g., intensity, fluence, wavelength, etc.) delivered to the skin, (g) one or more color/pigment sensor for detecting the color or level of pigmentation in the skin, (h) one or more treatment endpoint sensor, e.g., a color/pigment sensor, for detecting an influence of the radiation on the skin (e.g., erythema, temperature, perifollicular edema, etc.) during or after a treatment, (i) one or more eye safety sensor for preventing unwanted eye exposure to light from laser(s) 15, (j) one or more dwell sensor for detecting if the device is stationary or essentially stationary with respect to the skin, (k) one or more roller-type sensors for detecting the displacement and/or glide speed of device 10, (l) one or more imaging sensors for determining pre-treatment skin condition such as texture or hair count for setting subsequent treatment parameters, and/or any (m) other suitable types of sensors.

User interfaces 28 may include any systems for facilitating user interaction with device 10. For example, user interfaces 28 may include buttons, switches, knobs, sliders, touch screens, keypads, devices for providing vibrations or other tactile feedback, speakers for providing audible instructions, beeps, or other audible tones; or any other methods for receiving commands, settings, or other input from a user and providing information or output to the user. User interfaces 28 may also include one or more displays 32, one or more of which may be touchscreens for receiving user input. One or more user interfaces 28 or portions thereof may be included in a separate housing from the treatment device, such as in a smart charging dock or a personal computer, and the treatment device may communicate with the separate housing via hardwire (such as a cable or jack), wireless methods (such as infrared signals, radio signals, or Bluetooth), or other suitable communication methods.

Power supplies 22 may include any one or more types and instances of power supplies or power sources for generating or supplying power to the various components of device 10. For example, power supplies 22 may comprise one or more rechargeable or non-rechargeable batteries, capacitors, super-capacitors, DC/DC adapters, AC/DC adapters, and/or connections for receiving power from an outlet (e.g., 110V wall outlet). In some embodiments, power supplies 22 include one or more rechargeable or non-rechargeable batteries, e.g., one or more Li containing cells or one or more A, AA, AAA, C, D, prismatic, or 9V rechargeable or non-rechargeable cells.

Figure 2:
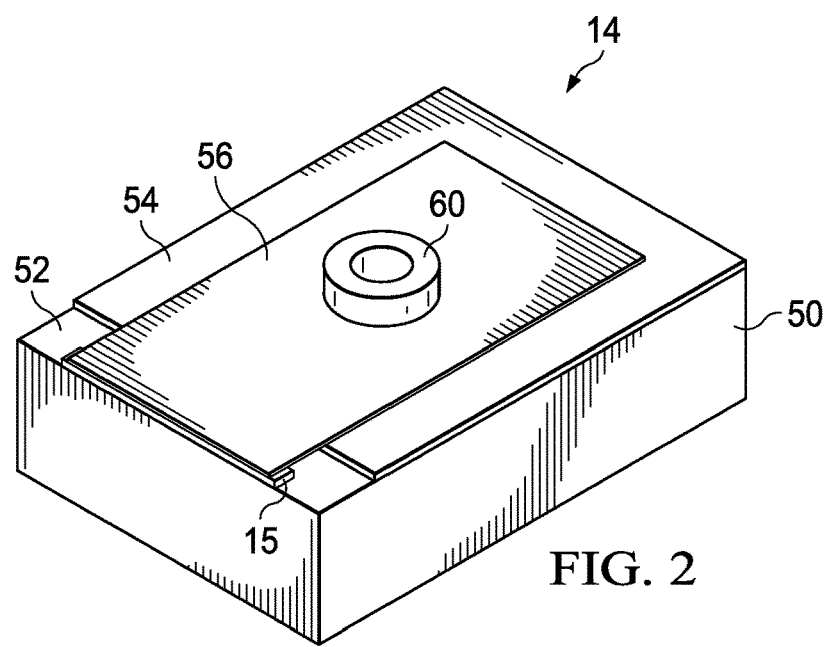
FIG. 2 illustrates an example configuration of a laser package, according to certain embodiments.

FIG. 2 illustrates one example configuration of laser package 14, according to certain embodiments. As shown, the structure of the laser package 14 includes an electrically and thermally conductive carrier 50 (also referred to as a "submont" or "substrate"), one or more semiconductor-based laser device 15 (hereafter referred to simply as "laser 15") mounted to a first region of a first side 52 of conductive carrier 50, an electrical insulation layer 54 arranged over a second region of the first side 52 of conductive carrier 50, an electrically conductive film 56 secured to laser 15 and extending over at least a portion of the insulation layer 54, such that insulation layer 54 is arranged between the conductive film 56 and conductive carrier 50, thereby electrically insulating conductive film 56 from conductive carrier 50. As shown, in some embodiments, laser package 14 may also include a shoulder washer 60 or other suitable structure(s) or elements(s) allowing laser package 14 to be secured to a heat sink and/or a printed circuit board without creating a short between conductive film 56 and conductive carrier 50 (e.g., by preventing contact between conductive film 56 and conductive carrier 50).

The conductive carrier 50 may serve both as a heat spreader for an attached heat sink 16, and as the anode of the laser 15. In some embodiments, the carrier 50 can be extended to become a complete integrated heatsink system (e.g., including integral or attached fins or other surface area-increasing structures), such that heat sink 16 is provided integral with laser package 14. The conductive foil 54 serves as the cathode contact of the laser 15 and may be attached the laser 15 in any suitable electrically conductive manner.

The components of laser package 14 may be assembled and secured in any suitable manner. In some embodiments, laser 15 is soldered on one side (e.g., the anode side) to carrier 50 and on the opposite side (e.g., the cathode side) to conductive film 56, either using a single soldering process or using two separate soldering processes (using the same or different solder materials for the separate solders). In other embodiments, laser 15 may be secured conductive carrier 50 and/or conductive film 56 may be secured to laser 15 by any suitable adhesive. In other embodiments, laser 15 may be held securely between conductive film 56 and conductive carrier 50 without soldering or adhesive. For example, laser 15 and conductive film 56 overlying laser 15 may be physically sandwiched between carrier 50 and another structure or layer to hold layer 15 and conductive film 56 in place.

In some embodiments, insulation layer 54 is secured to carrier 50 by adhesive, conductive epoxy, thermal grease, or mechanical pressure. In particular embodiments, insulation layer 54 is an adhesive tape applied to surface 52 of carrier 50. In other embodiments, insulation layer 54 is not affixed to carrier 50, but held securely against carrier 50 by other structure(s) or layer(s). For example, insulation layer 54 may be physically sandwiched between carrier 50 and another structure or layer (which may also cover conductive film 56 or portions thereof) to hold insulation layer 54 in place.

As discussed above, conductive film 56 may be secured to laser 15 by solder, adhesive, or other suitable manner. In some embodiments, conductive film 56 is also secured to the underlying insulation layer 54, e.g., by solder, adhesive, or other suitable manner. In other embodiments, conductive film 56 is not secured to the underlying insulation layer 54, but may be held in place by any suitable structure(s) or layer(s). For example, as discussed below with reference to FIGS. 5A-5B, conductive film 56 may be held against the underlying insulation layer 54 by a lead contact structure (e.g., spacer 156) between a printed circuit board and the laser package 14 that provides an electrically conductive path from laser 15 (e.g., cathode side), through conductive film 56, through the lead contact, and to the PCB.

In some embodiments, conductive carrier 50 has a coefficient of thermal expansion that does not match a coefficient of thermal expansion of the laser 15 mounted thereon. In this disclosure, two coefficients of thermal expansion (CTEs) "match" if they differ by 20% or less, and do not match (or "mismatch") if they differ by more than 20%. Thus, in some embodiments, the respective CTEs of conductive carrier 50 and laser 15 differ by more than 20%. For example, the respective CTEs of conductive carrier 50 and laser 15 may differ by an amount between 20% and 500%. In some embodiments, the respective CTEs of conductive carrier 50 and laser 15 differ by more than 100%. In particular embodiments, the respective CTEs of conductive carrier 50 and laser 15 differ by more than 200%.

For example, in embodiments that include a GaAs laser 15, the respective CTEs of conductive carrier 50 and laser 15 may differ by an amount between about 20% and 350%. As examples only, a Cu conductive carrier 50 may provide a CTE mismatch with the GaAs laser of about 200% to 250%, and an Al conductive carrier 50 may provide a CTE mismatch with the GaAs laser of about 300% to 350%.

As another example, in embodiments that include an InP laser 15, the respective CTEs of conductive carrier 50 and laser 15 may differ by an amount between about 300% and 500%. As examples only, a Cu conductive carrier 50 may provide a CTE mismatch with the InP laser of about 300% to 400%, and an Al conductive carrier 50 may provide a CTE mismatch with the InP laser of about 450% to 500%.

Example details of some example embodiments having the configuration shown in FIG. 2 are now discussed. Conductive carrier 50 may be formed from aluminum or copper, which may be plated with nickel or other suitable material for facilitating soldering. As discussed above, carrier 50 may serve as a heat spreader for an attached heat sink 16, as well as the anode of the laser 15. Or, carrier 50 may be formed as an integrated heatsink system (e.g., including integral or attached fins or other surface area-increasing structures), such that heat sink 16 is provided integral with laser package 14.

A laser 15 with the anode side (p-side) down is soldered onto surface 52 of carrier 50. In some embodiments, the laser 15 includes one or more laser diode bars or single-emitter laser diodes. In a particular embodiment, e.g., for a laser hair removal device, laser 15 is an approximately 1 cm long laser diode bar or fraction of a bar.

The conductive film 56 may be a copper foil attached to the cathode side (n-side) of the laser 15 via solder or other electrically conductive means, and thus acts as the cathode contact for the laser 15. The insulation layer 54 may be arranged between the aluminum or copper carrier 50 and copper foil 54 to electrically isolate the anode (carrier 50) and cathode (foil 54) from each other. Insulation layer 54 may be made of Kapton (polyimide) tape, shim, or film, a ceramic layer, a dielectric deposited film, or other readily available and low cost materials that can withstand the relevant soldering temperature(s).

A shoulder washer 60 formed from an insulating material protrudes through respective openings formed in the foil 54 and insulation layer 54 and partially into the carrier 50. The insulative washer 60 may allow the laser package 14 to be secured to a separate heat sink 16 by a screw (extending through respective openings formed in the carrier 50 and heat sink 16) without shorting the foil 54 and carrier 50. The washer 60 may also function as a spacer between the laser package 14 and printed circuit board, e.g., to provide a proper spacing for one or more lead contacts extending between the PCB and laser package 14 (e.g., to provide conductive paths between electronics on the PCB and the copper film 56 (cathode) and/or carrier 50 (anode). In some embodiments, the PCB may also be secured to the laser package 14 by a screw extending through washer 60. In one example embodiment, a screw may extend through the PCB, through laser package 14 (and through washer 60), and into or though heat sink 16, to secure these components to each other.

Figure 3:
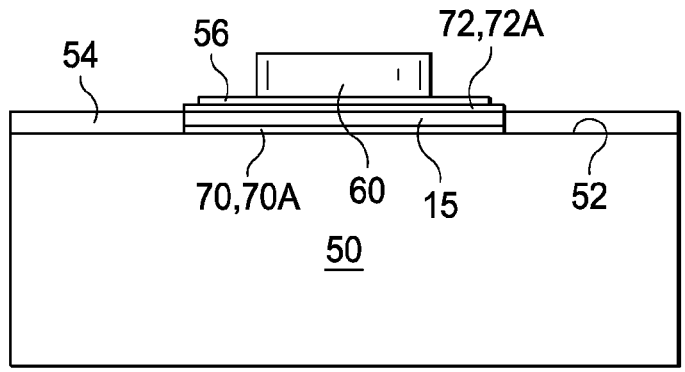
FIG. 3 illustrates a side view of the example laser package shown in FIG. 2, according to an embodiment in which the laser is soldered between a conductive carrier and a conductive film.

FIG. 3 illustrates a side view of the example laser package 14 shown in FIG. 2, according to an embodiment in which laser 15 is soldered between carrier 50 and conductive film 56. As shown, laser 15 is soldered to surface 52 of carrier 50 by a first solder connection 70 formed by a heating a first solder preform 70A formed on surface 52. Further, conductive film 56 is soldered to laser 15 by a second solder connection 72 formed by a heating a second solder preform 72A formed on laser 15. FIG. 3 also shows the locations of insulative film 54 and washer 60. It should be understood that the components are not shown to scale in FIG. 3. In particular, the thickness of certain layers is exaggerated in order to illustrate the relative positions of the components.

In some embodiments, e.g., as discussed below with reference to the example method of FIG. 4, the first and second solder connections 70 and 72 may be formed in one step, by assembling the structure with both the first and second solder preforms 70A and 72A as shown, and then heating the assembled structure in a single step such that solder connections 70 and 72 are formed simultaneously from solder preforms 70A and 72A. In such embodiments, first and second solder preforms 70A and 72A may be formed from the same material or from different materials. One or both of the first and second solder preforms 70A and 72A may be formed from a material with a melting temperature above 160° C., such as a tin-lead alloy (melting temperature range=180° C.-200° C.), tin-lead-bismuth (melting temperature range=160° C.-180° C.), tin-lead-silver (melting temperature range=180° C.-210° C.). Thus, in some embodiments, one or both of the first and second solder preforms 70A and 72A are not Indium-based. In one particular embodiment, first and second solder preforms 70A and 72A are tin-lead alloys, which are assembled on either side of laser 15 as shown in FIG. 3, and then heated together in a single step to form solder connections 70 and 72. Alternatively, one solder preform 70A or 72A may be formed from a material with a melting temperature above 160° C. (e.g., tin-lead alloy), while the other is formed from a material with a melting temperature below 160° C. (e.g., Indium or an Indium-based alloy), and both may still be heated in one step (based on the higher melting temperature) to form solder connections 70 and 72 simultaneously.

In other embodiments, first and second solder connections 70 and 72 may be formed in separate steps. For example, first solder connection 70 may be formed by heating first solder preform 70A in a first step, and second solder connection 72 may be formed by forming and heating second solder preform 72A in subsequent processing steps. In such embodiments, the second solder preform 72A may be formed from a lower-temperature solder material than the first solder preform 70A, such that the second solder preform 72A can be heated to form the second solder 72 at a lower temperature that does not melt the previously formed first solder connection 70. Both solder preforms 70A and 72A may have a melting temperature above 160° C., with preform 72A having the lower melting temperature. For example, preform 70A may be formed from Sn(63%)/Pb (37%), while preform 72A is formed from In(52%)/Sn (48%). Alternatively, preform 70A may be formed from a material with a melting temperature above 160° C. (e.g., tin-lead alloy), while preform 72A is formed from a material with a melting temperature below 160° C. (e.g., Indium or an Indium-based alloy), such that the first solder connection 70 may be formed in a first process, and second solder connection 72 may be formed in a subsequent, lower-temperature process.

Each of first and second solder connections 70 and 72 may have any suitable thickness, e.g., by using solder preforms 70A and 72A of suitable dimensions and/or using selected solder processing parameters (e.g., temperature, heating duration, etc.). For example, in some embodiment, first solder connection 70 between laser 15 and carrier 50 has a thickness of between 10 μm and 100 μm, and in particular embodiments, between 10 μm and 50 μm. Thus, solder connection 70 may be sufficiently thick to avoid any problems caused by surface roughness (e.g., typically up to about 1 μm) and/or flatness variations (e.g., typically up to about 10 μm) of the underlying carrier 50, e.g., formed from aluminum or copper. In some embodiments, second solder connection 72 between conductive film 56 and laser 15 has a thickness of between 20 μm and 200 μm.

Figure 4:
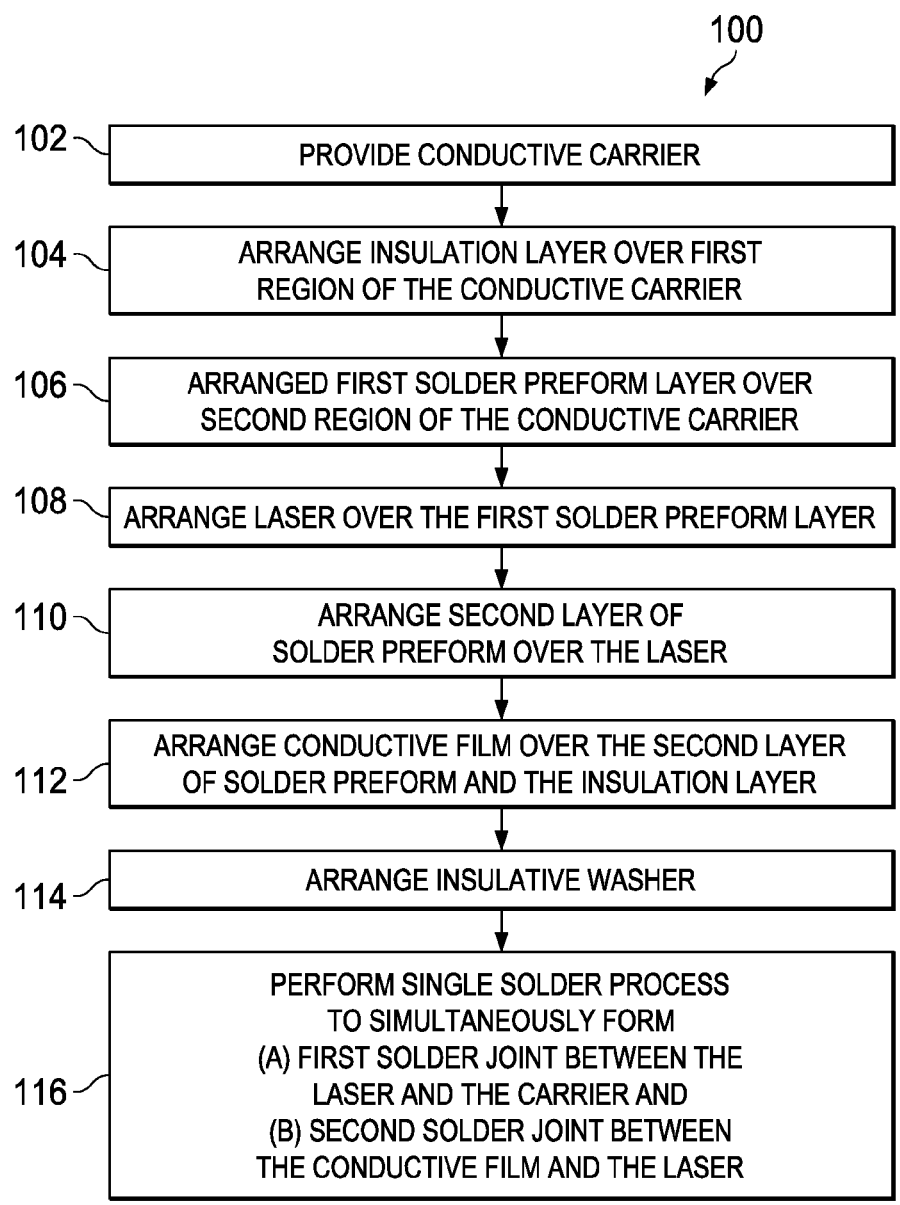
FIG. 4 illustrates an example method for assembling the laser package shown in FIGS. 2 and 3, according to certain embodiments.

FIG. 4 illustrates an example method 100 for assembling the laser package 14 shown in FIGS. 2 and 3, according to certain embodiments. At step 102, a conductive carrier 50 is provided. In example embodiments, the conductive carrier 50 may be formed from aluminum or copper, and may be nickel plated for enhanced solderabilty.

At step 104, an insulation layer 54 is arranged over a first region of a first side 52 of the carrier 50. In one embodiment, insulation layer 54 is a Kapton tape and this step comprises applying an adhesive side of the tape to the surface of carrier 50.

At step 106, a first solder preform layer 70A is formed or arranged over the first side 52 of carrier 50. In one embodiment, first solder preform layer 70A is a tin-lead alloy sliver with a thickness of between 10 μm and 50 μm, e.g., between 20 and 35 μm.

At step 108, laser 15 is arranged on the first solder preform layer 70A. In one embodiment, laser 15 is a laser diode bar or partial laser diode bar with an length of about 1 cm. In other embodiments, laser 15 comprises multiple single-emitter laser diodes, or multiple laser diode bars.

At step 110, a second layer of solder preform 72A is formed or arranged over the laser 15. In one embodiment, first solder preform layer 72A is a tin-lead alloy sliver with a thickness of between 20 μm and 200 μm.

At step 112, a conductive film 54 is arranged over the second layer of solder preform 72A and over at least a portion of the insulation layer 54, such that the insulation layer 54 physically separates the conductive film 54 from the underlying carrier 50. In one embodiment, conductive film 54 is a copper film having a thickness of between 10 μm and 200 μm, e.g., about 75 μm.

At step 114, an insulative washer 60 is arranged through respective openings formed in the conductive foil 54 and insulation layer 54 and partially into the carrier 50. In some embodiments, washer 60 may instead be added after the solder heating step 116, e.g., where washer 60 has a lower melting temperature than the soldering temperature.

At step 116, the assembled laser package 14 is heated to form first and solder joints 70 and 72 from solder preforms 70A and 72A, respectively, in a single heating process.

Figure 5A:
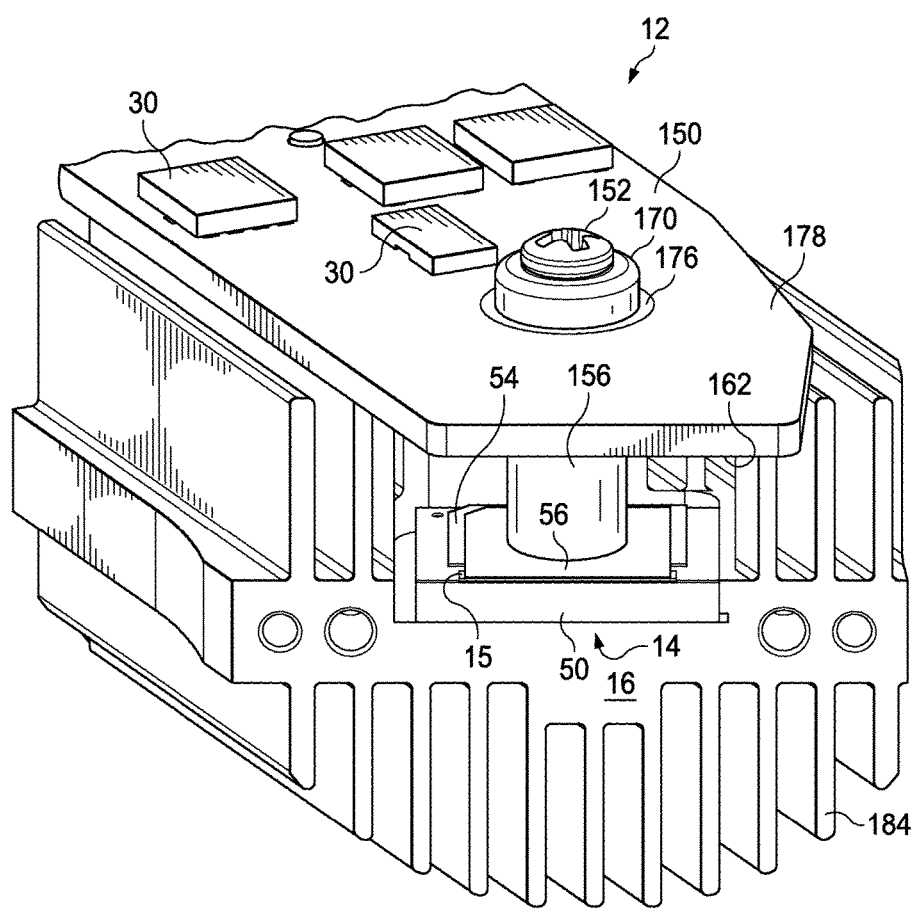
FIG. 5A shows a first three-dimensional cross-sectional view of an assembled laser engine including a laser package similar to the example shown in FIGS. 2 and 3, according to an example embodiment.
Figure 5B:
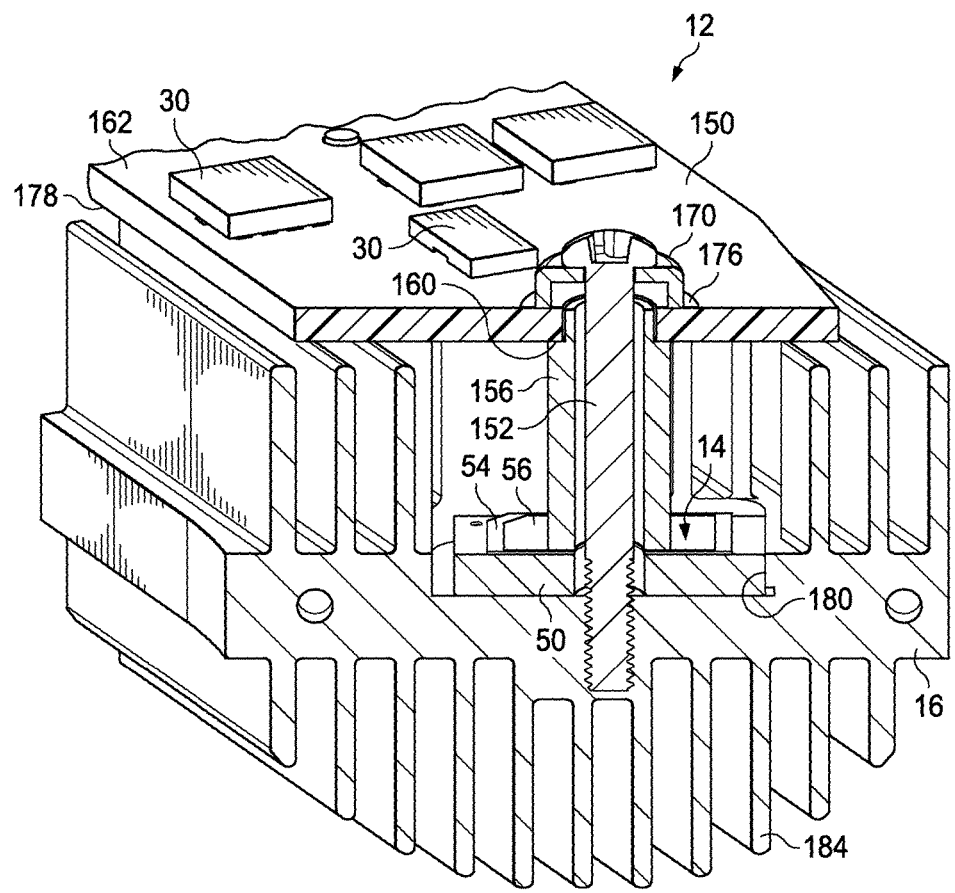
FIG. 5B shows a second three-dimensional cross-sectional view of the assembled laser engine shown in FIG. 5A.

FIGS. 5A and 5B show an example of an assembled laser engine 12, according to one example embodiment. In particular, FIG. 5A shows a three-dimensional cross-sectional view through a plane passing through the front surface of the laser package 14, while FIG. 5B shows a three-dimensional cross-sectional view through a plane passing through a connection screw 152 and through an interior of the laser package 14.

As shown, the example laser engine 12 includes a laser package 14, a heat sink 16, and a printed circuit board 150, all secured by a screw 152. Laser package 14 may have a design similar to that shown in FIGS. 2 and 3, and assembled in the manner described in the method of FIG. 4. In particular, laser package 14 includes a laser diode bar 15 mounted on a conductive carrier 50, an electrical insulation layer 54 arranged on the conductive carrier 50, and an electrically conductive film 56 secured to the top surface of the laser diode bar 15 and extending over a portion of the insulation layer 54, such that insulation layer 54 physically separates, and thereby electrically insulates, conductive film 56 from conductive carrier 50.

As shown, an electrically conductive spacer 156 may be arranged between laser package 14 and printed circuit board 150. A first surface of conductive spacer 156 at or near a first end of spacer 156 is pressed against conductive film 56, and a second surface of conductive spacer 156 (in this embodiment, defined by a stepped structure of spacer 156) is pressed against a conductive surface, area, or element 160 on a first side 162 of PCB 150. Thus, conductive spacer 156 defines an electrically conductive path between PCB 150 and conductive film 56, to thereby conduct electricity from the cathode side of laser diode bar 15 (to which conductive film 56 is secured) to circuitry on PCB 150.

Conductive spacer 156 may be hollow or otherwise include an opening 166 for receiving screw 152, which passes through a conductive washer/spacer element 170, through the opening 166 in spacer 156, and into heat sink 16, to thereby secure PCB 150 to laser package 14, and laser package 14 to heat sink 16. Screw 152 is electrically conductive, and cooperates with conductive spacer 156 to provide a complete electrical path through laser package 14. In particular, the head of screw 152 is compressed against conductive washer/spacer element 170, which is pressed against a conductive surface, area, or element 176 on a second side 178 of PCB 150, and the opposite threaded end of screw 152 is received in a threaded opening formed in heat sink 16. The conductive heat sink 16 is electrically coupled to the anode side of laser diode bar 15 via the electrically conductive carrier 50. Thus, screw 152 defines an electrically conductive path between PCB 150 and laser diode bar 15, to thereby conduct electricity from circuitry on PCB 150 to the anode side of laser diode bar 15 via heat sink 15 and conductive carrier 50.

In some embodiments, conductive surfaces, areas, or elements 160 and 176 may comprise electrical contacts are directly integrated onto the PCB 150. For example, electrical contacts 160 and 176 may comprise soldered lead contacts for making contact with spacer 156 and screw 152, respectively.

As shown in FIG. 5B, screw 152 is spaced apart from, and thus electrically isolated from, conductive spacer 156, to allow a complete circuit and prevent a short circuit. In some embodiments, this spacing may be provided by the respective alignment of the various components. In other embodiments, spacing components may be provided to further ensure that screw 152 and spacer 156 remain isolated. For example, an insulation washer 60 as shown in FIG. 2 may be arranged between screw 152 and spacer 156, with screw 152 extending through the washer 60 and spacer 156 arranged concentrically around the washer 60, to ensure isolation of screw 152 from spacer 156.

As shown, laser package 14 may be arranged in a recess 180 defined in heat sink 16, to increase the area of contact between conductive carrier 50 and heat sink 16, to promote heat transfer into heat sink 16. Thus, not only the bottom surface of carrier 50, but also one, two, or more side or other surfaces of carrier 50, may be physically mated against corresponding surfaces of heat sink 16, to increase heat transfer from carrier 50 to heat sink 16. Heat sink 16 may include fins 184 or any other surface-area-increasing shapes or structures.

Figure 6B:
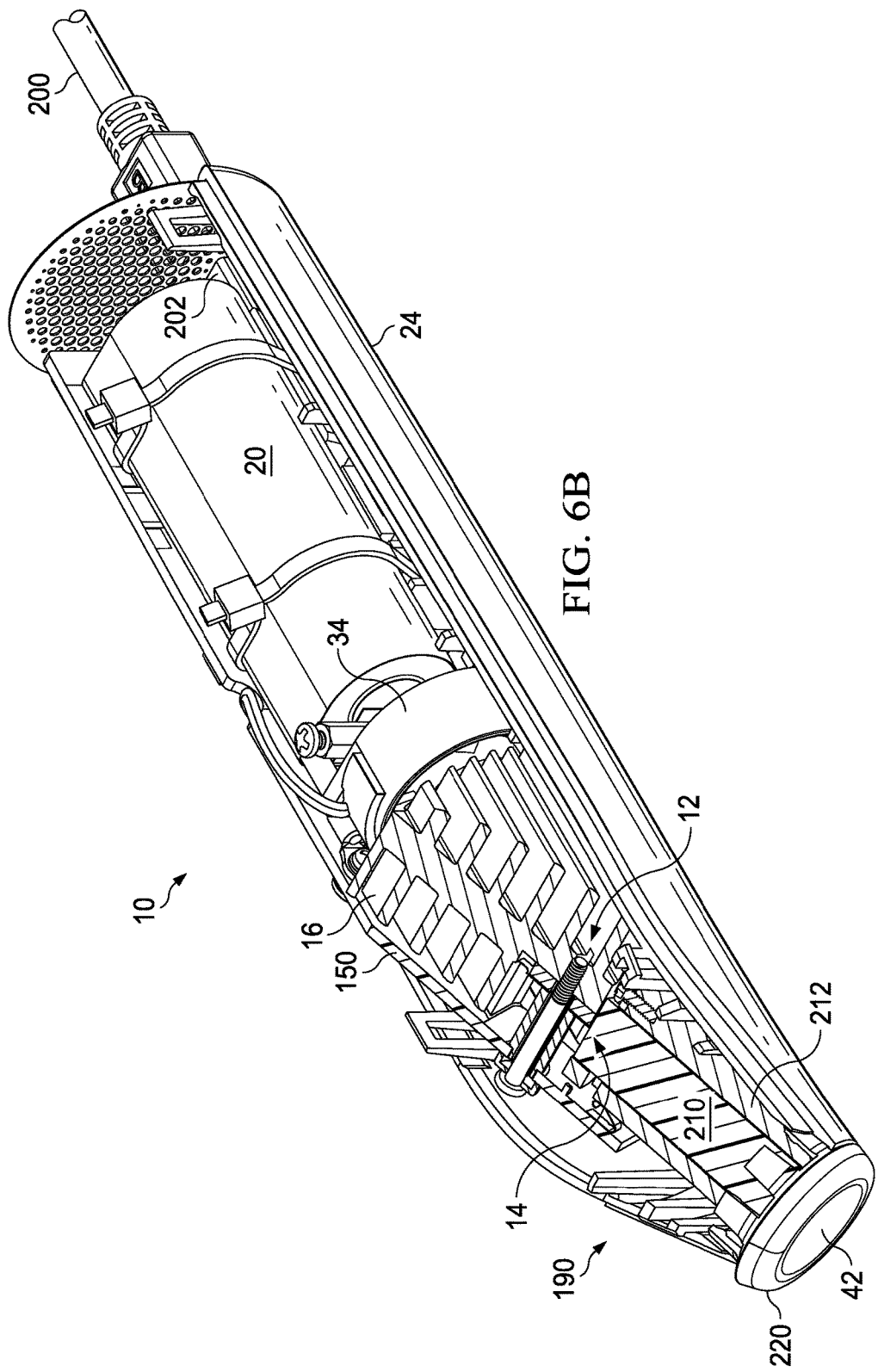

FIGS. 6A-6C show an example laser hair removal device 10 including the example laser engine shown in FIGS. 5A and 5B. In particular, FIG. 6A shows device 10 with the outer housing partially removed, to show internal components of the device 10; FIG. 6B is similar to the view of FIG. 6A, but with an angled cross-sectional cut through the front portion of the device to show internal details of the light engine 12 and other components near the device tip; and FIG. 6C is a close-up view of the front portion of the device shown in FIG. 6B.

As shown in FIGS. 6A-6C, device 10 includes a light engine 12, a light delivery/tip system 190 arranged forward of the light engine 12, and a fan 34 and battery 20 arranged rearward of the light engine 12, all arranged in an outer housing 24. As discussed above with respect to FIGS. 5A and 5B, light engine 12 includes a laser package 16 with a laser 15 (e.g., a diode laser or diode laser bar) mounted to a heat sink 16 and a printed circuit board 150 by a screw 152. The light delivery/tip system 190 may include a mixer (e.g., lightguide) 210, a barrel heatsink 212 extending around the mixer 210, a connecting bracket 214, and a tip insert 220 that connects to the outer housing 24 and defines an application end 42 having an opening 44 through which the forward end of mixer 210 is received. In some embodiments, the forward end of mixer 210 may form the leading surface through which radiation is emitted out of the application end 42 of device 10. In other embodiments, a diffuser or other optic(s) may be arranged downstream of the forward end of mixer 210 to define the leading surface through which radiation is emitted out of the device 10.

Mixer/lightguide 210 may be formed from plastic (e.g., PMMA/acrylic), glass, or other transparent material. Barrel heatsink 212, like heatsink 16, may be formed from any thermally conductive material or materials, e.g., aluminum or copper, and may include fins or any other surface-area-increasing shapes or structures. Connecting bracket 214 may be configured to align the laser submount 50 relative to the input end of mixer 210, and also for mechanically holding the mixer 210. Connecting bracket 214 may be formed from plastic (e.g., clear polycarbonate) or any other suitable material.

Device 10 also includes a DC power supply connection 202 providing an external connection for receiving a removable power cable 200 that may be connected to a wall outlet or other power source, such that battery 20 can be recharged via power cable 200 and then disconnected and used as a wireless handheld device. Power cable 200 may be connected to DC power supply connection 202 via any suitable type of connection, e.g., a USB or micro-USB connector, a cylindrical/barrel connector, a Kycon connector, etc.

Device 10 may deliver radiation as continuous wave (CW) radiation, manually pulsed radiation, automatically pulsed radiation, or in any other manner, and according to any suitable parameters, e.g., wavelength, current, power level, etc. For example, a wavelength of about 650 nm to about 1100 nm (e.g., about 810 in some applications) may be used for hair removal treatment. Further, device 10 may be configured for operation in a manual gliding mode, a stamping mode, or both, depending on the particular embodiment.

In some embodiments, control electronics 30 control laser 15 to provide CW or quasi-CW radiation, e.g., for operating device 10 in a gliding mode. In other embodiments, control electronics 30 control laser 15 to provide pulsed radiation. Pulsed radiation may include manually pulsed radiation or automatically pulsed radiation. In manually pulsed radiation, each pulse may be manually triggered, e.g., by pressing a button to initiate each pulse. In some embodiments, manually pulsed radiation used in a stamping mode. Alternatively, in automatically pulsed radiation, pulses may be initiated or controlled automatically, e.g., according to a predefined pulse frequency or automatically upon some triggering event, such as automatic pulse triggering upon a predetermined displacement of device 10 moving across the skin, or automatic pulse triggering upon re-triggering of a capacitive skin contact sensor by lifting and placing the device tip on a different spot, for example. Automatically pulsed radiation may be provided in any suitable manner, e.g., by controlling laser 15, by intermittently blocking the energy beam emitted by laser 15, or otherwise. Such embodiments may utilize any suitable pulse parameters, e.g., pulse rate or frequency, pulse on time, pulse off time, duty cycle, pulse profile, etc. In some embodiments, laser 15 may be pulsed at a rate between 0.3 and 75 Hz. For example, laser 15 may be pulsed at a rate between 2 and 30 Hz. In particular embodiments, laser 15 may be pulsed at a rate between 10 and 20 Hz, e.g., about 15 Hz. The energy per pulse on a given treatment zone can be achieved by a single pulse or by multiple repetitive pulses. Automatically pulsed radiation may be used for any suitable treatment, e.g., laser hair removal or fractional treatment.

As used herein, a "pulse" may include both (a) a single, continuous burst of radiation from laser 15, and (b) one or more higher-frequency pulses at substantially the same location on the skin (i.e., with substantially overlapping areas of irradiation at the skin surface), sometimes referred to as a modulated pulse, pulse train, or super pulse. If the time interval between the pulses in a pulse train is shorter than the relaxation time of the mechanism of action (e.g., shorter than the thermal relaxation time of a photothermolysis chromophore target), then the pulse train can deliver substantially similar results as a single longer pulse.

Further, at least some embodiments of device 10 provide eye safe radiation. For example, the emitted radiation from device 10 may be inherently eye safe, e.g., based on the divergence of laser radiation emitted from the application end 42 of device 10, the wavelength of such radiation, the pulse length, and/or other parameters of the emitted radiation. For example, in some embodiments or settings, device 10 the emitted radiation from device 10 meets the Class 1M or better (such as Class 1) eye safety classification per the IEC 60825-1. In addition, device 10 may provide a further layer of eye safety by incorporating an eye safety control system including one or more skin contact sensors, cornea-recognition sensors, etc., and suitable control electronics 30 for activating laser 15 only when the application end of the device is in contact with skin.

Prototype Testing

Prototype devices that embody various disclosed features and concepts were constructed and tested. In particular, the prototype devices were subjected to temperature cycling. The optical output and pulse droop of each tested prototype device were characterized, and a step stress lifetest was performed. A summary of results for these tests are discussed below.

Example Temperature Cycling:

Three laser packages built with laser diode bars mounted to aluminum carriers by tin-lead solder were placed into a convection oven while the oven was at 100° C. Once the laser package reached 100° C. it was allowed to soak for 10 minutes. The laser package was then removed and allowed to cool to room temperature. Once at room temperature, the laser package was put into a freezer at −80° C. Once the laser package reached −80° C., it was allowed to soak for 10 minutes. The laser package was then removed and allowed to cool to room temperature. This hot-cold cycle was repeated five times. After each cycle the package was inspected for signs of bar cracking of the laser diode bar. No bar cracking was observed in any of the laser diode bars.

Example Energy and Pulse Droop Measurements:

A control laser package ("control laser package") and a laser package according to the present disclosure ("inventive laser package") were constructed and tested at various currents and pulse widths (pulse durations).

Both the control laser package and the inventive laser package included an off-the-shelf 1 cm×1 mm laser diode bar (manufactured by Oclaro Inc.) mounted to a conductive carrier/submount. In the control laser package, the laser diode bar was mounted to a CuW carrier by a PbSn solder connection. The cathode contact to the circuit board was provided by a spring contact biased against a metalized BeO ceramic block soldered to the CuW carrier. The CuW carrier is CTE-matched with the semiconductor laser diode bar, i.e., the laser diode bar and carrier have a CTE difference of less than 20%, in particular about 15%

The inventive laser package was constructed according to the process 100 shown in FIG. 4, using a Cu carrier and a GaAs laser diode bar, thus providing a CTE mismatch with the laser diode bar, i.e., the laser diode bar and carrier have a CTE difference of greater than 20%, in particular about 240%. A first side (anode) of the laser diode bar was soldered to the underlying carrier by a first tin-lead solder and the opposite side (cathode) of the laser diode bar was soldered to an overlying copper foil (cathode contact) by a second tin-lead solder. The two solder connections were formed in a single heating process.

Tables 1 and 2 show the pulse energy/power and in-pulse droop due to junction heating at the laser bar. As shown, the pulse energy/power and in-pulse droop for the inventive laser package using non-CTE-matched materials are generally comparable to those of the more complicated control laser package using CTE-matched materials. The laser engine performance and reliability are more than adequate for common dermatological treatment devices, e.g., a battery-powered handheld hair removal laser device.

TABLE 1

Test parameters and results for the control laser package

| Current (A) | Voltage (V) | Pulse width (ms) | Energy (J) | Peak power | Signal max (mV) | Signal min (mV) | % drop |
|---|---|---|---|---|---|---|---|
| 40 | 1.8 | 300 | 12 | 40.0 | 134 | 130 | 3.0 |
| 40 | 1.8 | 400 | 16 | 40.0 | 134 | 130 | 3.0 |
| 40 | 1.8 | 500 | 20 | 40.0 | 134 | 130 | 3.0 |
| 50 | 1.8 | 300 | 15.5 | 51.7 | 134 | 130 | 3.0 |
| 50 | 1.8 | 400 | 20.8 | 52.0 | 134 | 130 | 3.0 |
| 50 | 1.8 | 500 | 25.8 | 51.6 | 137 | 134 | 2.2 |
| 60 | 1.8 | 300 | 19.1 | 63.7 | 139 | 135 | 2.9 |
| 60 | 1.8 | 400 | 25.5 | 63.8 | 139 | 134 | 3.6 |
| 60 | 1.8 | 500 | 31.7 | 63.4 | 139 | 134 | 3.6 |

TABLE 2

Test parameters and results for the inventive laser package

| Current (A) | Voltage (V) | Pulse width (ms) | Energy (J) | Peak power | Signal max (mV) | Signal min (mV) | % drop |
|---|---|---|---|---|---|---|---|
| 40 | 1.64 | 300 | 11.5 | 38.3 | 134 | 125 | 6.7 |
| 40 | 1.64 | 400 | 15.1 | 37.8 | 120 | 110 | 8.3 |
| 40 | 1.64 | 500 | 19 | 38.0 | 126 | 115 | 8.7 |
| 50 | 1.64 | 300 | 14.8 | 49.3 | 117 | 108 | 7.7 |
| 50 | 1.64 | 400 | 19.7 | 49.3 | 117 | 108 | 7.7 |
| 50 | 1.64 | 500 | 24.5 | 49.0 | 116 | 106 | 8.6 |
| 60 | 1.64 | 300 | 17.8 | 59.3 | 115 | 102 | 11.3 |
| 60 | 1.64 | 400 | 23.5 | 58.8 | 115 | 99 | 13.9 |
| 60 | 1.64 | 500 | 29.1 | 58.2 | 114 | 98.4 | 13.7 |

Figure 7:
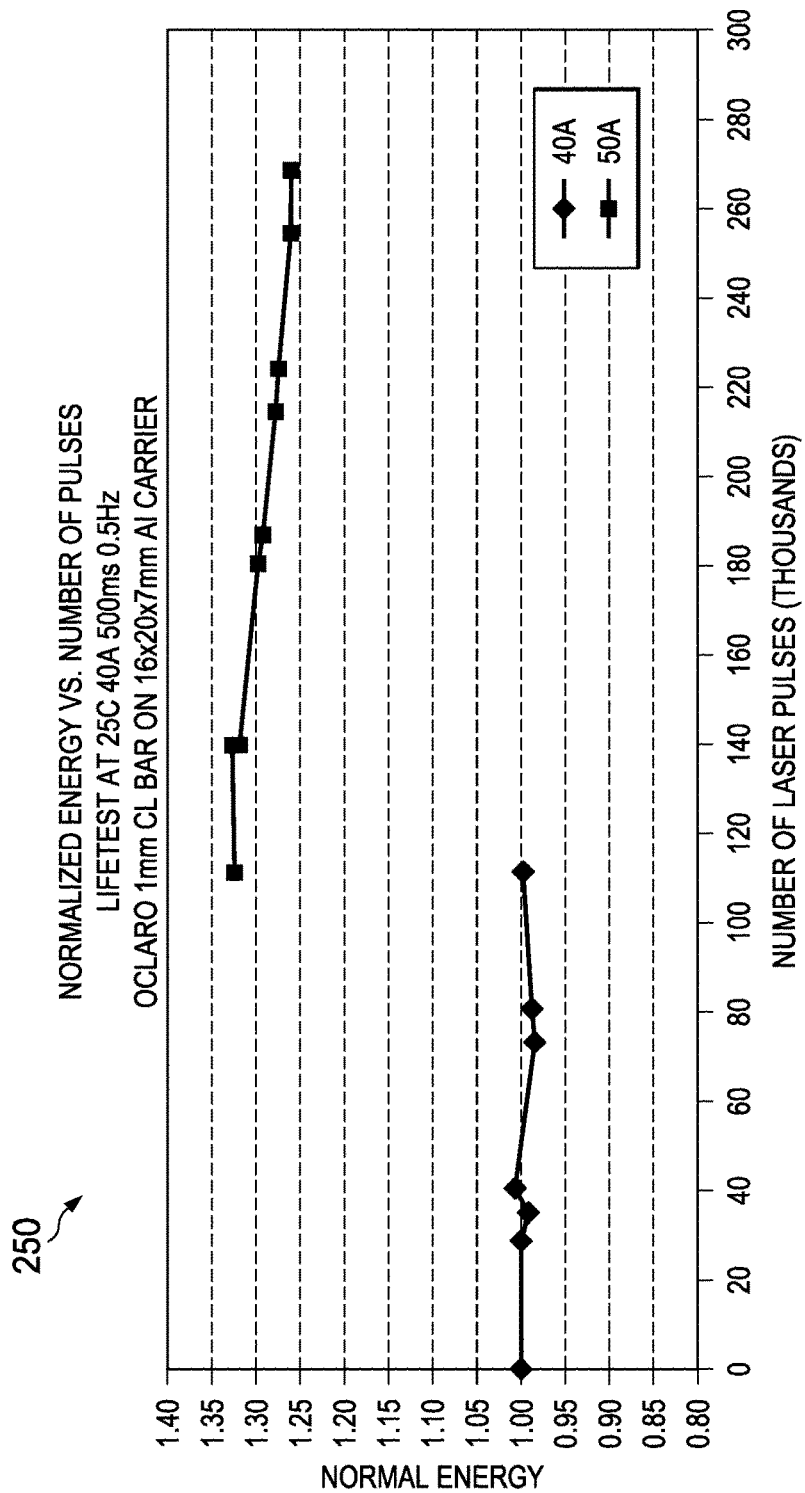
FIG. 7 shows example results of operational life testing of a pulsed laser diode bar mounted in a laser package according to teachings of the present disclosure.

Finally, FIG. 7 shows example results of operational life testing of a pulsed laser diode bar mounted in a laser package according to teachings of the present disclosure. In particular, the laser package was constructed according to the process 100 shown in FIG. 4, using a GaAs laser diode bar soldered to a Cu stamp carrier mounted to an Al heat sink (using thermal grease), thus providing a CTE mismatch between the laser diode bar and the Cu stamp carrier of between 200% and 250%. A first side (anode) of the laser diode bar was soldered to the underlying Cu stamp carrier by a first tin-lead solder and the opposite side (cathode) of the laser diode bar was soldered to an overlying copper foil (cathode contact) by a second tin-lead solder. The two solder connections were formed in a single heating process.

As shown in FIG. 7, the non-CTE matched laser package was life tested first with 40 A drive current up to 115 k pulses, showing negligible power degradation. The life test current was then increased to 50 A to complete the entire accelerated reliability testing to almost 280 k pulses, again with minimal corresponding power degradation.

Although the disclosed embodiments are described in detail in the present disclosure, it should be understood that various changes, substitutions and alterations can be made to the embodiments without departing from their spirit and scope.

The invention claimed is:

1. A dermatological treatment device, comprising:
a power supply; and
a laser package comprising:
an electrically conductive carrier having a first coefficient of thermal expansion;
an insulation layer arranged over a first region of a first side of the electrically conductive carrier;
a semiconductor laser device mounted to a second region of the first side of the electrically conductive carrier, the semiconductor laser device having a second coefficient of thermal expansion; and
an electrically conductive and physically continuous film including:
(a) a first planar surface region extending over a planar surface of the insulation layer opposite the electrically conductive carrier, such that the electrically conductive film is insulated from the electrically conductive carrier by the insulation layer; and
(b) a second planar surface region covering and secured directly to the semiconductor laser device; such that the electrically conductive and physically continuous film extends in a continuous manner over both the insulation layer opposite the electrically conductive carrier and the semiconductor laser device;
wherein the first coefficient of thermal expansion exceeds the second coefficient of thermal expansion by more than 20%; and
wherein the semiconductor laser device is electrically coupled to the power supply via the electrically conductive carrier and the electrically conductive film.

2. The dermatological treatment device according to claim 1, wherein the semiconductor laser device is mounted to the first side of the carrier by a solder having a melting temperature above 160° C.

3. The dermatological treatment device according to claim 1, wherein the semiconductor laser device is mounted to the first side of the carrier by non-Indium solder.

4. The dermatological treatment device according to claim 1, wherein the first coefficient of thermal expansion exceeds the second coefficient of thermal expansion by more than 100%.

5. The dermatological treatment device according to claim 1, wherein:
the semiconductor laser device is secured to the first side of the electrically conductive carrier by a first solder material, and
the second planar surface region of the electrically conductive film extends over, and is secured directly to the semiconductor laser device by the first solder material, such that the semiconductor laser device is sandwiched between the electrically conductive film and the second planar surface region of the electrically conductive carrier.

6. The dermatological treatment device according to claim 5, wherein:
the semiconductor laser device has an anode side and an opposing cathode side;
the anode side of the semiconductor laser device is mounted to the first side of the electrically conductive carrier; and
the second planar surface region of the electrically conductive film extends over, and is secured directly to, the cathode side of the semiconductor laser device.

7. The dermatological treatment device according to claim 1, further comprising a printed circuit board;
wherein the power supply is electrically coupled to the semiconductor laser device via the printed circuit board;
wherein the printed circuit board is coupled to the semiconductor laser device for providing power to the semiconductor laser device via solder-free connection.

8. The dermatological treatment device according to claim 1, further comprising:
control electronics coupled to the power supply and the laser package and configured to pulse the semiconductor laser device with a pulse duration of between 100 ms and 1000 ms.

9. The dermatological treatment device according to claim 1, wherein the device is free of any lens downstream of the laser device.

10. The dermatological treatment device according to claim 1, wherein the laser package includes exactly one electrically conductive film secured to the semiconductor laser device and having the planar surface extending over the planar surface of the insulation layer opposite the electrically conductive carrier.

11. The dermatological treatment device according to claim 1, wherein the first planar surface region and the second planar surface region of the electrically conductive film are connected to each other by an intermediate planar surface region of the electrically conductive film and not by a wire bond.

12. The dermatological treatment device according to claim 1, wherein the first planar surface region and the second planar surface region of the electrically conductive film lie in a common plane of the electrically conductive film.

13. A laser package for use in a dermatological treatment device, the laser package comprising:
   an electrically conductive carrier having a first coefficient of thermal expansion;
   an insulation layer arranged over a first region of a first side of the electrically conductive carrier;
   a semiconductor laser device mounted to a second region of the first side of the electrically conductive carrier, the semiconductor laser device having a second coefficient of thermal expansion; and
   an electrically conductive and physically continuous film secured to the semiconductor laser device and having a planar surface extending over a planar surface of the insulation layer opposite the electrically conductive carrier, such that the electrically conductive and physically continuous film is insulated from the electrically conductive carrier by the insulation layer;
   wherein the semiconductor laser device is sandwiched between the electrically conductive and physically continuous film and the electrically conductive carrier, such that the electrically conductive and physically continuous film extends in a continuous manner over both the insulation layer opposite the electrically conductive carrier and the semiconductor laser device; and
   wherein the first coefficient of thermal expansion exceeds the second coefficient of thermal expansion by more than 20%.

14. The laser package according to claim 13, wherein the semiconductor laser device is mounted to the first side of the carrier by a solder having a melting temperature above 160° C.

15. The laser package according to claim 13, wherein the semiconductor laser device is mounted to the first side of the carrier by non-Indium solder.

16. The laser package according to claim 13, wherein the first coefficient of thermal expansion exceeds the second coefficient of thermal expansion by more than 100%.

17. The laser package according to claim 13, wherein:
   the semiconductor laser device is secured to the first side of the electrically conductive carrier by a first solder material, and
   the electrically conductive film is secured to the semiconductor laser device by the first solder material.

18. The laser package according to claim 13, wherein:
   the semiconductor laser device has an anode side and an opposing cathode side;
   the anode side of the semiconductor laser device is mounted to the first side of the electrically conductive carrier; and
   the electrically conductive film is secured directly to the cathode side of the semiconductor laser device.

19. The laser package according to claim 13, wherein the electrically conductive film includes:
   a first portion extending over the insulation layer; and
   a second portion extending over the semiconductor laser device.

* * * * *